(12) United States Patent
Robl et al.

(10) Patent No.: US 8,858,581 B2
(45) Date of Patent: Oct. 14, 2014

(54) INTERFACE UNIT FOR POSITIONING AN OBJECT TO BE IRRADIATED IN RELATION TO A RADIATION SOURCE

(75) Inventors: Gerhard Robl, Stein (DE); Thomas Deisinger, Zirndorf (DE); Klaus Vogler, Eschenau (DE)

(73) Assignee: Wavelight GmbH (DE)

( * ) Notice: Subject to any disclaimer, the term of this patent is extended or adjusted under 35 U.S.C. 154(b) by 271 days.

(21) Appl. No.: 12/894,356

(22) Filed: Sep. 30, 2010

(65) Prior Publication Data

US 2012/0083774 A1 Apr. 5, 2012

(51) Int. Cl.
  *A61F 9/00* (2006.01)
  *A61B 18/18* (2006.01)
  *A61F 9/009* (2006.01)

(52) U.S. Cl.
  CPC ...................................... *A61F 9/009* (2013.01)
  USPC .............................................. 606/166; 606/4

(58) Field of Classification Search
  USPC .......... 606/4–6, 10–12, 166–170; 607/88–93; 128/898
  See application file for complete search history.

(56) References Cited

U.S. PATENT DOCUMENTS

| | | | |
|---|---|---|---|
| 5,549,632 A | 8/1996 | Lai | |
| 6,899,707 B2 | 5/2005 | Scholler et al. | |
| 8,235,973 B2 | 8/2012 | Vogler et al. | |
| 8,425,494 B2 | 4/2013 | Muhlhoff et al. | |
| 2002/0103482 A1* | 8/2002 | Scholler et al. | 606/5 |
| 2004/0036839 A1 | 2/2004 | Fischer et al. | |
| 2006/0195078 A1* | 8/2006 | Webb et al. | 606/5 |
| 2007/0093795 A1 | 4/2007 | Melcher et al. | |
| 2007/0179478 A1 | 8/2007 | Dobschal et al. | |
| 2007/0253083 A1 | 11/2007 | Muhlhoff et al. | |
| 2010/0228236 A1* | 9/2010 | Muhlhoff et al. | 606/4 |
| 2011/0009851 A1* | 1/2011 | Donitzky et al. | 606/4 |

FOREIGN PATENT DOCUMENTS

| | | |
|---|---|---|
| DE | 10052068 A1 | 5/2002 |
| DE | 102006056711 A1 | 6/2008 |
| EP | 1891915 A1 | 8/2006 |
| EP | 1844745 A2 | 10/2007 |
| WO | 2010022745 A1 | 3/2010 |

* cited by examiner

*Primary Examiner* — Ahmed Farah

(57) ABSTRACT

An interface unit for positioning an object to be irradiated in relation to a radiation source has at least one first positioning surface for positioning the interface unit in relation to the radiation source, and a second positioning surface for bearing on the object to be irradiated. The interface unit provides a path, which passes through the second positioning surface, for the radiation from the radiation source. According to the invention, the interface unit comprises an integrally produced interface body which forms both the at least one first positioning surface and the second positioning surface. The interface body is preferably produced from a plastic material by an injection compression molding method, in order to achieve the desired high manufacturing accuracy.

14 Claims, 3 Drawing Sheets

INTERFACE UNIT FOR POSITIONING AN OBJECT TO BE IRRADIATED IN RELATION TO A RADIATION SOURCE

The invention relates to an interface unit for positioning an object to be irradiated in relation to a radiation source, the interface unit having at least one first positioning surface for positioning the interface unit in relation to the radiation source, and a second positioning surface for bearing on the object to be irradiated, the interface unit providing a path which passes through the second positioning surface for the radiation from the radiation source.

BACKGROUND OF THE INVENTION

Such an interface unit may, for example, be used for laser surgical cutting operations on the human eye. The interface unit, which in the case of a human object to be irradiated may also be referred to as a patient interface, is used in this case to establish positionally fixed coupling between the patient's eye and the laser system which provides the laser radiation, usually between the eye and a focusing objective of laser system. Fixed coupling is necessary in order to maintain a constant distance between the focusing objective and the patient's eye, so that the cut can be made with the desired high precision in the eye's tissue portion to be processed, for example the cornea.

For cutting operations not only eye tissue but also other biological tissue, as well as dead material, it is known per se to use so-called laser-induced optical breakdown. By applying focused laser radiation, such breakdown is created in the focal region when there is a sufficient spatial and temporal energy density of the pulses, lying above the breakdown threshold. Optical breakdown causes substantially athermic local destruction of the tissue being treated. This effect is referred to as photodisruption. By sequencing such photodisruptions, virtually any desired three-dimensional cutting pattern can be produced in the tissue being processed. Typically, laser systems having laser radiation pulse durations in the femtosecond range are nowadays used for cutting operations. For these ultrashort pulse durations, the breakdown threshold is comparatively low, which is conducive to low radiation exposure of the tissue being treated. The size of the photodisruption is essentially limited to the extent of the radiation focus. The cutting precision therefore depends crucially on the spatial adjustment accuracy of the focus.

It is possible to reference the eye's front surface in relation to the coordinate system of the laser system by using an interface unit of the type considered here. However, manufacturing tolerances of the interface unit, which can be manifested as tolerances of the optical properties of the interface unit, cause corresponding deviations of the focal position in the tissue being treated. The cutting precision therefore depends crucially on the manufacturing precision of the interface unit. A high manufacturing accuracy of the interface unit is therefore extremely desirable.

The interface unit may for example have a sleeve-like spacer piece and an optical window arranged on one end, in which case the laser radiation travels along the sleeve axis through the inner region of the spacer piece, passes through the window and then emerges from the interface unit. The outer side of the window is used for the object to be treated to bear on, for example the eye to be treated. The laser radiation therefore enters the material to be treated directly from the window. Correspondingly, the outer side of the window forms a positioning surface for positioning the object to be irradiated. On the other end of the sleeve from the window, the interface unit is furthermore equipped with suitable positioning structures for axial positioning of the interface unit in relation to the laser system. The spacer piece may for example be configured in the shape of a cylindrical sleeve; solutions in which a conical sleeve shape is selected for the spacer piece are known in the prior art, the window being provided at the narrow end of the cone. In these solutions, the spacer piece may be referred to as a spacer cone; it is to be understood that a conical shape for the spacer piece is in no way compulsory in the scope of the invention.

One way of manufacturing an interface unit configured in the above manner, with a spacer piece and a window for the radiation to pass through, consists in making the spacer piece from a metallic material, for example aluminium, and, for the window, fitting a glass plate which satisfies the optical requirements into a frame in the spacer piece and adhesively bonding it therein. Such a manufacturing method, however, places stringent requirements on compliance with permissible tolerances, because the individual manufacturing tolerances of the spacer piece and the glass plate can add together, and the adhesive bonding process can furthermore be another source of inaccuracies.

BRIEF SUMMARY OF THE INVENTION

It is an object of the invention to be able to produce an interface unit of the type referred to in the introduction with high accuracy.

In order to achieve this object, the invention proposes that the interface unit should comprise an integrally produced interface body which forms both the at least one first positioning surface and the second positioning surface. In this way it is possible to avoid assembly inaccuracies, of which there would otherwise be a risk if the at least one first positioning surface is provided on a first sub-body and the second positioning surface is provided on a second, separately manufactured sub-body, and the two sub-bodies need to be adhesively bonded together or firmly connected in another way. The tolerance chain to be taken into account when producing the interface unit from separate sub-bodies, made up of the manufacturing accuracy of each one of the sub-bodies and the assembly accuracy when connecting the sub-bodies, can be reduced by the solution according to the invention to any manufacturing inaccuracies of the monobloc interface body. Addition of a plurality of individual tolerances can be avoided. This applies not only to the geometrical dimensions of the interface unit, but also to its optical properties (optical path lengths).

The at least one first positioning surface defines a reference surface of the interface unit on the radiation input side, while the second positioning surface defines a reference surface on the radiation output side. The path provided for the radiation by the interface unit extends in the direction from the radiation input reference surface to the radiation output reference surface. Along this path, the radiation travels through at least two mediums with different optical densities, and in a simple and expedient configuration one of the mediums is air and the other medium may be the material of a radiation-transparent window element forming the second positioning surface.

In one embodiment, the interface body is made of a material which is suitable for an injection moulding method, preferably an injection compression moulding method, this material preferably being a plastic material. The plastic material may for example comprise a cyclo-olefin copolymer, a cyclo-olefin polymer, polycarbonate or polymethyl methacrylate. It is to be understood that these mentions of materials are purely exemplary, and other injection-mouldable, in particular biocompatible plastic materials are possible.

Preferably, at least a part of the interface body is transparent in the visible wavelength range. Such transparency of the interface body is expedient in particular for a part of the interface body which forms a spacer piece enclosing the radiation path. The transparency makes it possible to avoid partial shadowing of the light from a light source used to illuminate the operation field. It is then even possible, when configuring the interface unit with a cylindrical or conical spacer piece, to make its circumferential surface continuous i.e. free from any openings.

According to one embodiment, the entire interface body may consist of the same material. According to an alternative configuration, the interface body may have various regions which respectively consist of different material. Even in this alternative configuration, however, the interface body is produced as one piece. When there are different regions of the interface body, which consist of different materials, integral production of the interface body is possible, for example, by injection moulding the various regions in the same production step in an injection mould. Modern multi-component injection moulding apparatus are capable of injection moulding components made of different materials. The scope of the invention furthermore does not exclude at least one sub-piece of the interface body being prefabricated and the other regions of the interface body then being injection moulded onto the prefabricated sub-piece, so as to create a material-fit connection. For example, it is feasible to use a prefabricated suction ring component, place it into an injection mould and then injection mould the remaining regions of the interface body onto the suction ring component. Preferably, at least one continuous section of the interface body, comprising the two positioning surfaces, in any event consists of the same material.

In a preferred embodiment, the interface body has a spacer cone enclosing the path for the radiation, and a contact element provided on the narrow end of the spacer cone for bearing on the object to be irradiated. The contact element forms the said window for the radiation output. It may have a contact surface, facing towards the eye, which is configured to be plane, concave or convex or has rounded edge regions. On its other side facing towards the radiation source (i.e. on the side facing away from the eye), the contact element may on the other hand be configured to be plane or with a freeform surface. A biplanar contact plate may for example be employed as the contact element, or a planoconcave or planoconvex contact element may be used on which the contact surface facing towards the eye is respectively concave or convex, and the opposite side facing away from the eye is configured to be plane. By configuring the contact element's side facing away from the eye as a freeform surface, when there is a non-planar configuration of the contact surface, it is possible to compensate for a focal degradation due to edge distortion (spherical aberrations). Particularly with an injection in moulding method, any desired configurations of such a freeform surface may be produced per se, so that the freeform surface can be configured optimally with a view to compensation for any aberrations which may be induced by a non-planar configuration of the contact surface.

Instead of a biplanar contact plate, it is possible to use a contact element configured application-specifically in another way, for example a planoconcave or planoconvex contact element and/or one with rounded edge surfaces. Instead of plane, the side of the contact plate facing towards the object to be irradiated may for example also be convex or rounded at the edge.

The contact element may be provided with a reflection-reducing coating on its side facing towards the eye and/or its side facing away from the eye, in order to reduce any reflection losses of the material of the interface body at the wavelength of the radiation being used.

It is known to use interface units with the functionality considered here, at least for ophthalmological operations, in conjunction with a suction ring which is first placed on the eye and then fixed there by suction force. The interface unit is subsequently brought close to the suction ring and made it to engage with it. In this way, not only is the eye fixed by the suction ring, but the interface unit is also positioned in relation to the suction ring, and in particular centred. In one embodiment of the invention, it is now feasible to configure the interface body with integrally formed structures which can fulfil the functionality of such a suction ring. Correspondingly, the interface unit may have at least one evacuation space which is at least partially open towards the object to be irradiated, for fixating the interface body by suction on the object to be irradiated. The use of a separate suction ring can then be obviated.

It has already been explained that the interface body may have various regions which respectively consist of different material. In an interface body which is equipped with the formations that a fulfil the function of a conventional suction ring, this concept may be used to form a continuous first section of the interface body, comprising the two positioning surfaces, from a different material than a second section of the interface body which forms such suction ring formations (for example an evacuation space). For example, the second section may consist of Macrolon or another plastic. The possibility that the second section consists of the metallic material is not in fact excluded.

According to a further aspect, the invention relates to a method for producing an interface unit of the type described above. The interface body is in this case produced by an injection compression moulding method. In injection compression moulding, the plastic melt is injected into the not yet fully closed injection moulding tool. The tool is not closed completely until during the solidification process. The closure pressure thereby built up ensures the definitive shaping of the moulded part. To that extent, it has a combined injection moulding-compression moulding method. It has been found that with an injection compression moulding method, plastic interface bodies can be produced in large batch numbers with the requisite optical quality at a comparatively economical cost, and above all with extraordinarily high manufacturing accuracy.

BRIEF DESCRIPTION OF THE DRAWINGS

The invention will be further explained below with the aid of the appended drawings, in which.

DETAILED DESCRIPTION OF PREFERRED EMBODIMENTS

Figure 1:
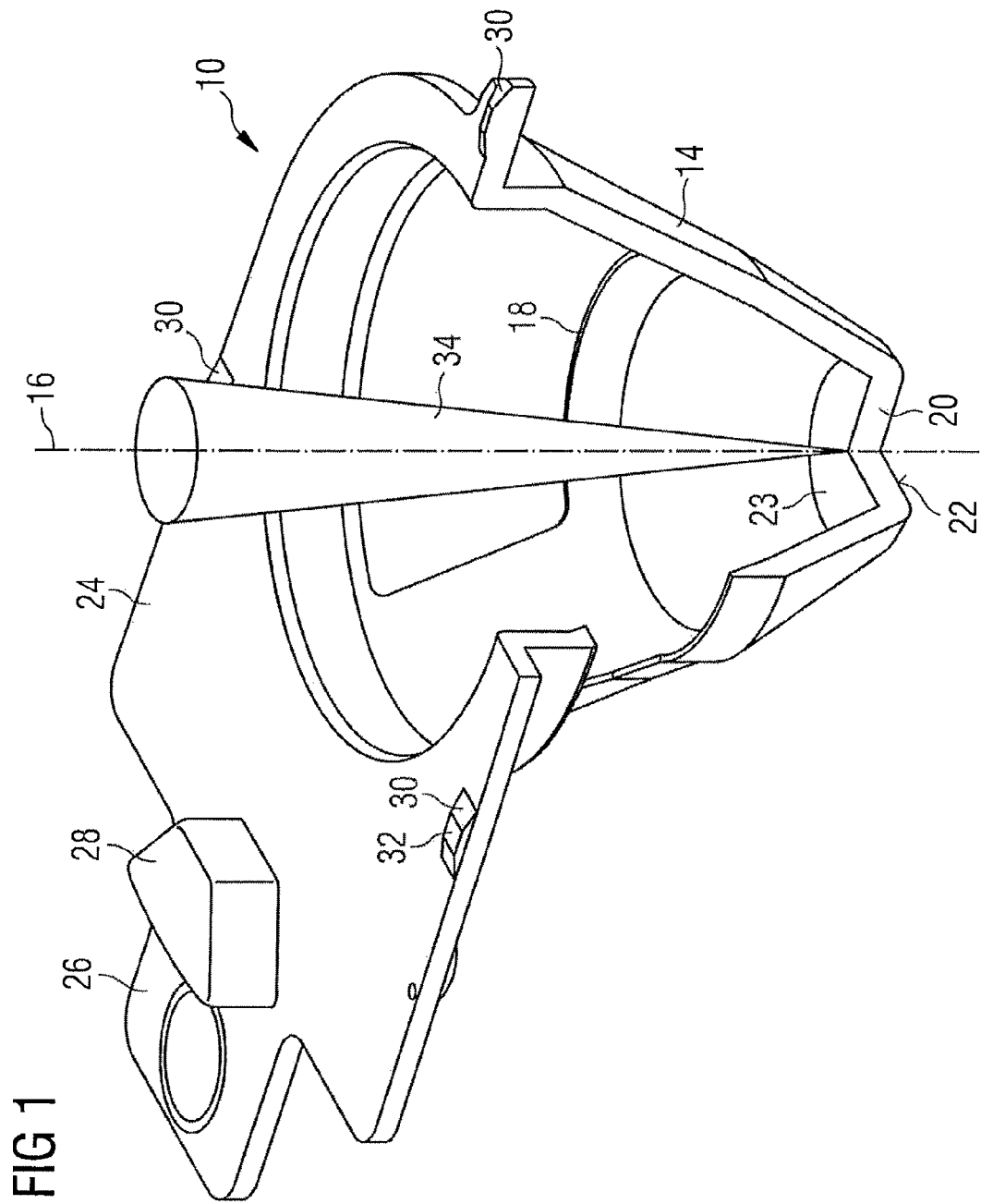
FIG. 1 represents an interface unit according to an embodiment in a partially cut-away perspective view.
Figure 2:
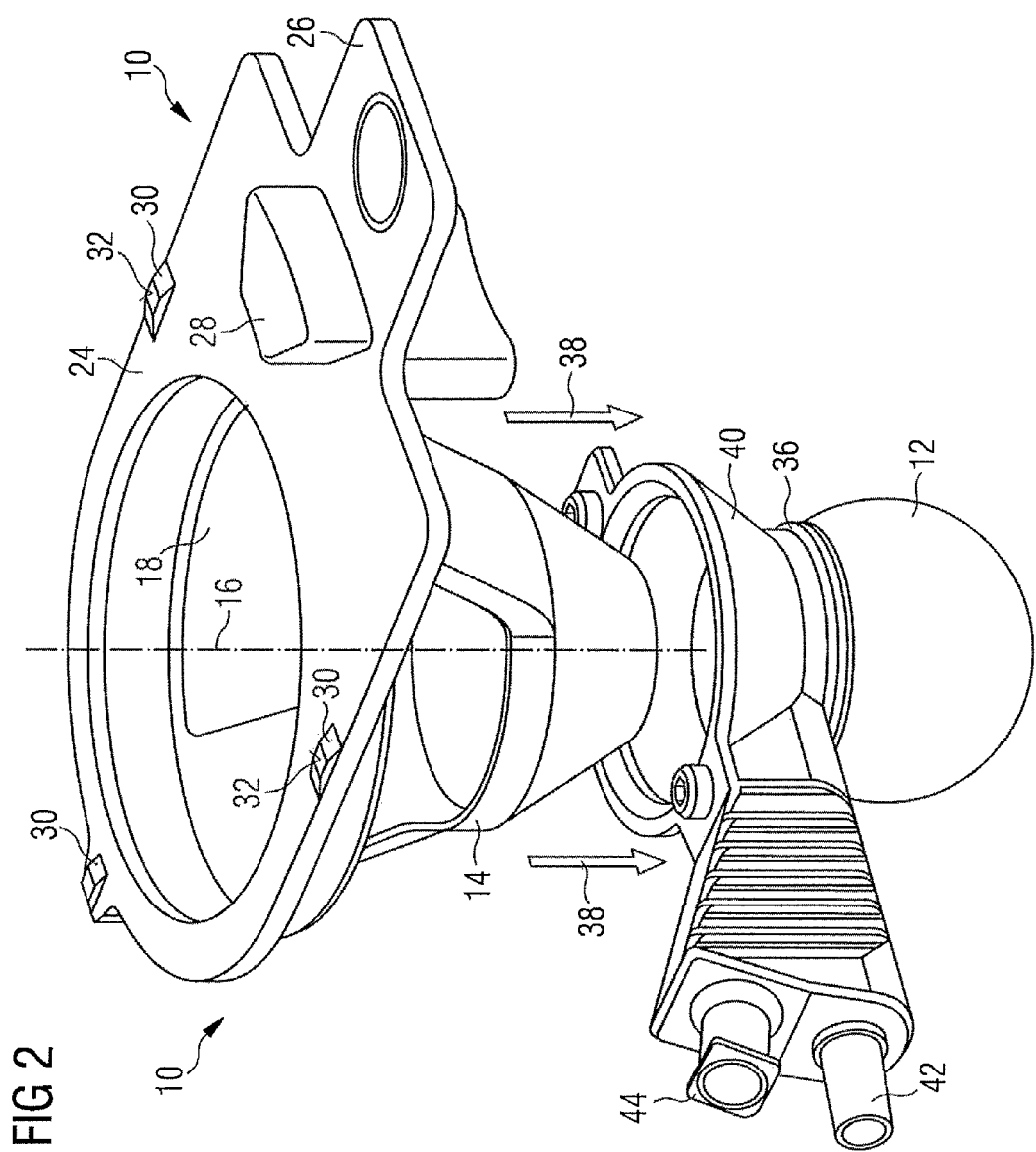
FIG. 2 represents the interface unit of FIG. 1 together with a suction ring unit placed on a human eye and FIG. 3 schematically represents an interface unit according to another embodiment.

Reference will first be made to FIGS. 1 and 2. They show an interface unit denoted overall by 10, which is used for coupling to a laser system (not represented in detail) and makes it possible to position and reference a human eye 12 to be treated in relation to the laser system. The interface unit 10 comprises the spacer cone 14 having a cone axis 16. The conical side surface of the spacer cone 14 has a plurality of openings 18 in the exemplary case shown; it is to be understood that the conical side surface may alternatively be configured as a side surface consisting of solid material.

When a spacer cone is referred to here, it is to be understood that neither the internal nor external circumferential surface of the cone necessarily has to form a conical surface exactly in the mathematical sense. Instead, when progressing in the axial direction, the conical side surface may readily have a plurality of notches, steps or bends. Overall, however, the spacer cone exhibits a conical general configuration by becoming increasingly wide, starting from one of its axial ends, in the direction of the other axial end.

It is to be understood that, in a variant, a cylindrical or differently shaped, internally hollow spacer body may be used instead of the spacer cone 14.

On the narrow end of the spacer cone 14, the interface unit 10 has a contact plate 20, here configured in a plane-parallel fashion, which forms a contact surface 22 for bearing on the surface of the eye 12 to be treated. The contact plate 20 is oriented orthogonally to the cone axis 16 and, owing to the planarity of its contact surface 22, is usually referred to in technical terminology as an applanation plate; it makes it possible to flatten the cornea of the eye 12.

The side of the contact plate 20 opposite to the contact surface 22 (i.e. the side facing away from the eye) is designated 23.

On the wide end of the spacer cone 14, the interface unit 10 is furthermore configured with a mounting flange 24, which extends annularly around the spacer cone 14 and protrudes radially from the spacer cone 14. Over a part of its circumferential extent, the mounting flange 24 is widened to form a gripping plate 26, which allows a user to grip the interface unit 10 and insert it radially into a slot (not represented in detail) of the laser system. The radial insertion depth may be limited by a projection 28, which is formed on the gripping plate 26 and interacts with a radial bearing flange (not represented in detail) of the laser system. In the slot, the interface unit 10 is fixed axially in relation to the laser system; suitable clamping elements, by means of which the mounting flange 24 can be clamped firmly in the slot, may be provided on the laser system if so desired.

On the upper side of the mounting flange 24, a total of three positioning projections 30 are provided, these being distributed at approximately equal angular spacings along the cone circumference and respectively forming an axially oriented positioning surface 32 on their upper side. When the interface unit 10 is being installed, the positioning surfaces 32 of the projections 30 enter into axially positioning engagement with an axial bearing surface of the laser system, so that fixed axial positioning of the interface unit 10 in relation to the laser system is provided by the mutual bearing of the positioning projections 30 on this bearing surface.

The interface unit 10 provides an access path for the laser radiation of the laser system 10, extending along the cone axis 16, as indicated by a focal ray bundle 34 in FIG. 1. The access path for the laser radiation extends through the contact plate 20. The positioning surfaces 32 of the positioning projections 30 respectively form a first positioning surface in the sense of the invention, whereas the contact surface 22 of the contact plate 20 forms a second positioning surface in the sense of the invention.

Because the interface unit 10 is often a disposable article for reasons of hygiene, particularly in the case of use for eye surgery treatments, users require a stock of interface units in order to be able to use a new interface unit for each operation. Replacement of the interface unit should not of course lead to the laser system having to be readjusted, i.e. the z position of the beam focus having to be re-referenced. This places correspondingly stringent requirements on the manufacturing accuracy of the interface unit 10, and above all on the axial (geometrical) distance of the positioning surfaces 32 from the contact surface 22 and on the thickness of the contact plate 20. Both the geometrical distance of the positioning surface 32 from the contact surface 22 and the axial thickness of the contact plate 20 influence the effective optical path lengths of the interface unit 10 when the bundle of rays 34 passes through the interface unit 10.

For high manufacturing precision, and correspondingly for high precision of the optical properties of the interface unit 10, in the exemplary case shown it is configured as a monobloc interface body, i.e. the spacer cone 14 is produced in one piece together with the contact plate 20 and the mounting flange 24. Owing to the transparency requirement for the contact plate 20, the material of this monobloc interface body is a material which is transparent to the laser radiation. The material of the interface body preferably also has a high, colour-neutral transparency in the visible wavelength range, in order to provide a sufficiently bright true-colour operation field for the doctor. A plastic injection moulding method is suitable for producing a comparatively complexly shaped structure such as the interface unit 10 in one piece, and the stringent accuracy requirements of the interface unit 10 can be fulfilled in particular by an injection compression moulding method. Here, injection compression moulding is intended to mean a method in which the plastic melt is injected into an enlarged cavity and compressed by mobile tool elements in the subsequent compression phase. Using the injection compression moulding technique, components can be produced with an optical quality which satisfies even the stringent requirements of laser systems for ophthalmological applications.

The plastic used to produce the interface unit 10 is expediently biocompatible. Suitable plastics, which can receive certification as biocompatible, are for example PMMA (polymethyl methacrylate), cyclo-olefin polymers, cyclo-olefin copolymers and polycarbonates. Examples of commercially available materials which are suitable for integral production of the interface unit 10 by an injection compression moulding method are Topas® from Topas Advanced Polymers and Zeonex® from Zeon Chemicals. It is to be understood that no restriction to one of these exemplary materials is intended; any plastic materials which are compatible with an injection compression moulding method and exhibit sufficient transmission at least at the wavelength of the laser radiation being used, and are furthermore sufficiently radiation-stable, may be used in principle.

In order to avoid reflection losses, it is recommendable to provide the integrally produced interface body with a reflection-reducing coating on at least one or both plate sides of the contact plate 20.

During use, in accordance with the representation of FIG. 2, the interface unit 10 is brought axially close to a suction ring unit 36 previously placed onto the eye 12 and fixed there (in a manner not represented in detail) by suction force, as indicated by two direction arrows 38. The spacer cone 14 is then introduced into a receiving funnel 40 of the suction ring unit 36 and is thereby centred in relation to the suction ring unit 36. A suction chamber may be delimited between the interface unit 10 and the suction ring unit 36, the evacuation of which leads to suction of the interface unit 10 onto the suction ring unit 36 and therefore to mutual fixing of these two components. In the course of introduction of the interface unit 10 into the receiving funnel 40 of the suction ring unit 36, the contact plate 20 can come to bear with its contact surface 22 on the surface of the eye; as an alternative, it is feasible that the contact plate 20 does not yet bear on the eye 12 when the interface unit 10 is in the fully introduced state, and in order to establish bearing contact between the eye 12 and the contact plate 20 it is first necessary to evacuate the space between them.

In the exemplary case shown, the suction ring unit 36 is configured with two connection glands 42, 44, which are respectively used for attachment to a tube line (not represented in detail) for connection to a pump system. Each of the connection glands 42, 44 is connected via an internal path system respectively to a suction chamber of the suction ring unit 36 so that these two suction chambers can be evacuated separately from one another.

Figure 3:
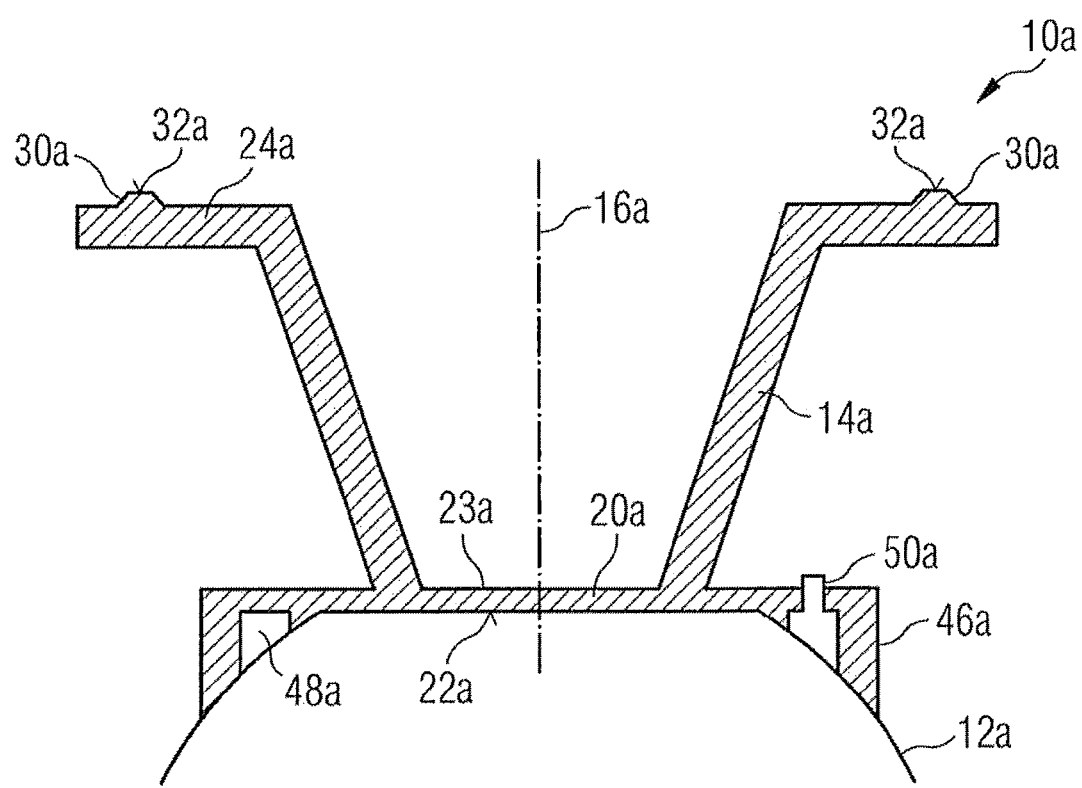

In the embodiment shown in FIG. 3, components which are the same or have the same effect are provided with the same references as before, but suffixed by a lower-case letter. In order to avoid unnecessary repetition, reference is made to that stated above in connection with the explanation of FIGS. 1 and 2, unless otherwise indicated below.

The interface unit 10*a* according to the embodiment of FIG. 3 is formed by an integrally produced interface body which forms not only the spacer cone 14*a*, the contact plate 20*a* and the mounting flange 24*a*, but also a suction ring 46*a* having a suction chamber 48*a* which is open towards the surface of the eye and is used to suck the suction ring 46*a* onto the eye 12*a*. The suction chamber 48*a* is configured here as an annular chamber, which is open towards the surface of the eye along its entire annular circumference and is connected to an evacuation connection, schematically indicated at 50*a*, to which a tube line (not represented in detail) can be attached in order to connect the interface unit 10*a* to a pump system. The interface unit 10*a* therefore combines the functions of a suction ring for fixing the eye 12*a*, the applanation of the cornea of the eye 12*a* and the axial positioning of the eye 12*a* in relation to the laser system. That which was stated above applies to the production of the interface unit 10*a*; it is produced from a transparent and biocompatible plastic material by an injection moulding method, in particular by an injection compression moulding method. In the scope of this injection moulding method, it is conceivable to use a different material for the suction ring 46*a* than for the other parts of the interface unit 10*a*, in particular the spacer cone 14*a*, the contact plate 20*a* and the mounting flange 24*a*. In this way, it is possible to produce an interface body which is monobloc but nevertheless has regions which respectively consist of different material. As an alternative, it is of course possible to manufacture the entire interface unit 10*a* from the same material.

The invention claimed is:

1. An interface unit for positioning an object to be irradiated in relation to a radiation source, the interface unit having:
    an upper side with a plurality of first positioning projections that project outwardly from the upper side, each first positioning projection having a first positioning surface, the first positioning surfaces configured to enter into axially positioning engagement with the radiation source for positioning the interface unit in relation to the radiation source, and
    a second positioning surface for bearing on the object to be irradiated, the interface unit providing a path which passes through the second positioning surface for the radiation from the radiation source,
    wherein the interface unit comprises an integrally produced interface body which forms both the first positioning surfaces and the second positioning surface.

2. An interface unit according to claim 1, wherein the interface body is made of a material which is suitable for an injection compression moulding method.

3. An interface unit according to claim 2, wherein the material is a plastic material.

4. An interface unit according to claim 2, wherein the plastic material comprises one of a cyclo-olefin copolymer, a cyclo-olefin polymer, polymethyl methacrylate and polycarbonate.

5. An interface unit according to claim 1, wherein at least a part of the interface body is transparent in the visible wavelength range.

6. An interface unit according to claim 1, wherein the interface body has various regions which respectively consist of different materials.

7. An interface unit according to claim 1, wherein at least one continuous section of the interface body, comprising the first and the second positioning surfaces, consists of the same material.

8. An interface unit according to claim 1, wherein the interface body has a spacer cone enclosing the path, and a contact element provided on a narrow end of the spacer cone for bearing on the object to be irradiated.

9. An interface unit according to claim 8, wherein the contact element has a contact surface, facing towards an eye, which is configured to be one of plane, concave, convex and with rounded edge regions.

10. An interface unit according to claim 9, wherein the contact element is configured to be one of plane and with a freeform surface on its other side from the contact surface.

11. An interface unit according to claim 10, wherein a continuous first section of the interface body, comprising the first and the second positioning surfaces, consists of a different material than a second section of the interface body which forms the evacuation space.

12. An interface unit according to claim 8, wherein the contact element is provided with a reflection-reducing coating on at least one of its side facing towards an eye and its side facing away from the eye.

13. An interface unit according to claim 1, wherein the interface unit has at least one evacuation space which is at least partially open towards the object to be irradiated, for fixating the interface body by suction on the object to be irradiated.

14. A method for producing an interface unit according to claim 1, wherein the interface body is produced by an injection compression moulding method.

* * * * *